US00PP27614P2

(12) United States Plant Patent
de Jong

(10) Patent No.: US PP27,614 P2
(45) Date of Patent: Jan. 24, 2017

(54) ***ASTRANTIA* PLANT NAMED 'STAR OF LOVE'**

(50) Latin Name: *Astrantia major*
Varietal Denomination: Star of Love

(71) Applicant: Jacobus Robertus de Jong, Noordwijkerhout (NL)

(72) Inventor: Jacobus Robertus de Jong, Noordwijkerhout (NL)

( * ) Notice: Subject to any disclaimer, the term of this patent is extended or adjusted under 35 U.S.C. 154(b) by 0 days.

(21) Appl. No.: 14/756,970

(22) Filed: Nov. 3, 2015

(51) Int. Cl.
*A01H 5/02* (2006.01)

(52) U.S. Cl.
USPC ..... Plt./408

(58) Field of Classification Search
USPC ..... Plt./408
See application file for complete search history.

*Primary Examiner* — Annette Para
(74) *Attorney, Agent, or Firm* — Penny J. Aguirre

(57) ABSTRACT

A new cultivar of *Astrantia* plant named, 'Star of Love', that is characterized by its strong, upright plant habit with well-branched inflorescences, its foliage that is healthy and dark green in color, its floriferous bloom habit, its inflorescences that are red-purple in color and produce high quality cut flowers, its re-blooming habit; blooming from May to June and again from August to October in The Netherlands.

2 Drawing Sheets

Botanical classification: *Astrantia major.*
Cultivar designation: 'Star of Love'.

BACKGROUND OF THE INVENTION

The present invention relates to a new and distinct cultivar of *Astrantia*, botanically known as *Astrantia major* 'Star of Love', and will be referred to hereafter by its cultivar name, 'Star of Love'. 'Star of Love' represents a new herbaceous perennial grown for landscape use and as a cut flower.

The new cultivar, 'Star of Love', was selected by the Inventor in May of 2010 as seedling growing in a trial plot in Noordwijkerhout, The Netherlands. The trail plot had been planted from seed collected from an open-pollinated proprietary plant of *Astrantia major* plant (not patented) from the Inventors breeding program.

Asexual propagation of the new cultivar was first accomplished by division by the Inventor in April of 2011 in Noordwijkerhout, The Netherlands. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Star of Love' as a unique cultivar of *Astrantia.*

1. 'Star of Love' exhibits a strong, upright plant habit with well-branched inflorescences.
2. 'Star of Love' exhibits foliage that is healthy and dark green in color.
2. 'Star of Love' exhibits a floriferous bloom habit.
3. 'Star of Love' exhibits inflorescences that are red-purple in color and produce high quality cut flowers.
4. 'Star of Love' exhibits a re-blooming habit; blooming from May to June and again from August to October in The Netherlands.

The female parent plant of 'Star of Love' differs from 'Star of Love' in having a weaker plant habit, in being less floriferous, and in having flowers that are lighter red in color. 'Star of Love' can be most closely compared to the *Astrantia* cultivars 'Claret' (not patented) and 'Primadonna' (not patented). Both cultivars are similar to 'Star of Love' in having flowers that are red in color. 'Claret' differs from 'Star of Love' in being shorter in plant height, in having foliage that is lighter green in color and shaped differently, and in having less densely branched inflorescences. 'Primadonna' differs from 'Star of Love' in having flowers that are lighter red in color, in having foliage that is lighter green in color and shaped differently, in having a less floriferous and shorter bloom period, and in having less densely branched inflorescences.

BRIEF DESCRIPTION OF THE DRAWINGS

The accompanying colored photographs illustrate the overall appearance and distinct characteristics of the new *Astrantia.* The photographs were taken of a two year-old plant of 'Star of Love' as field grown in De Hoef, The Netherlands and placed in a container for the photographs.

The photograph in FIG. 1 provides a side view of a plant of 'Star of Love' in bloom.

Figure 1:
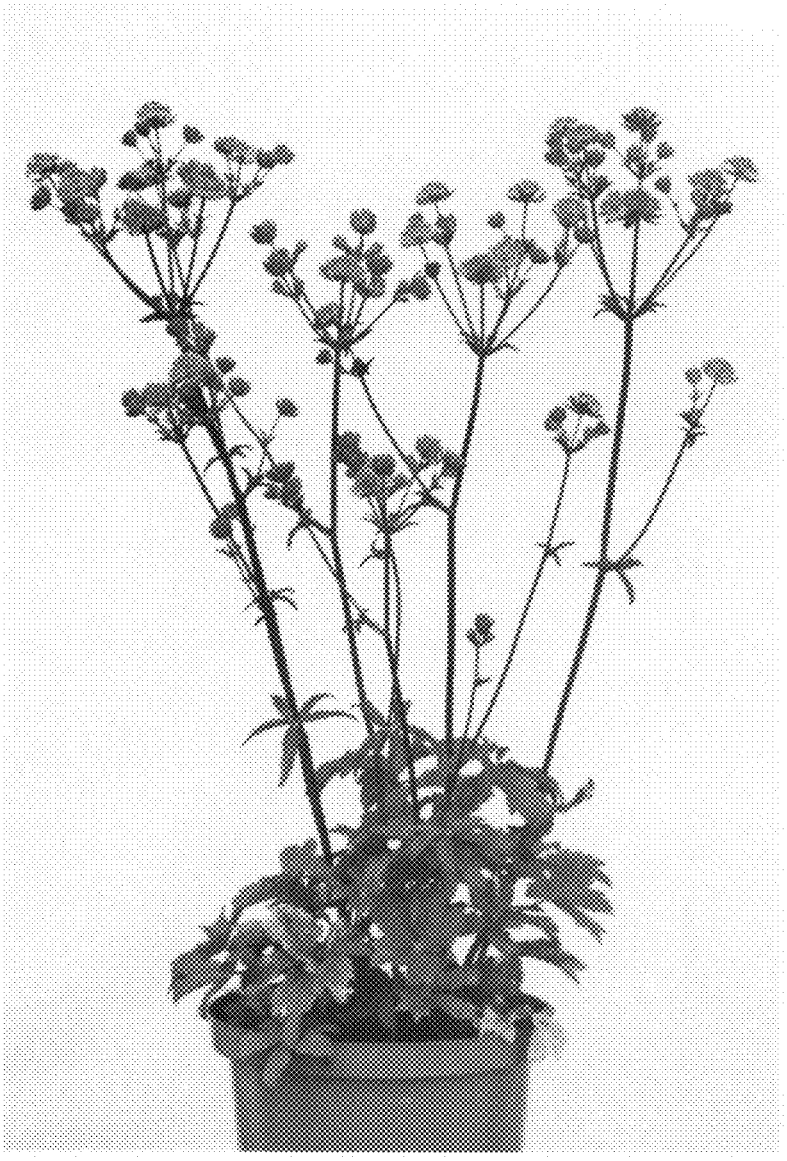
Figure 2:
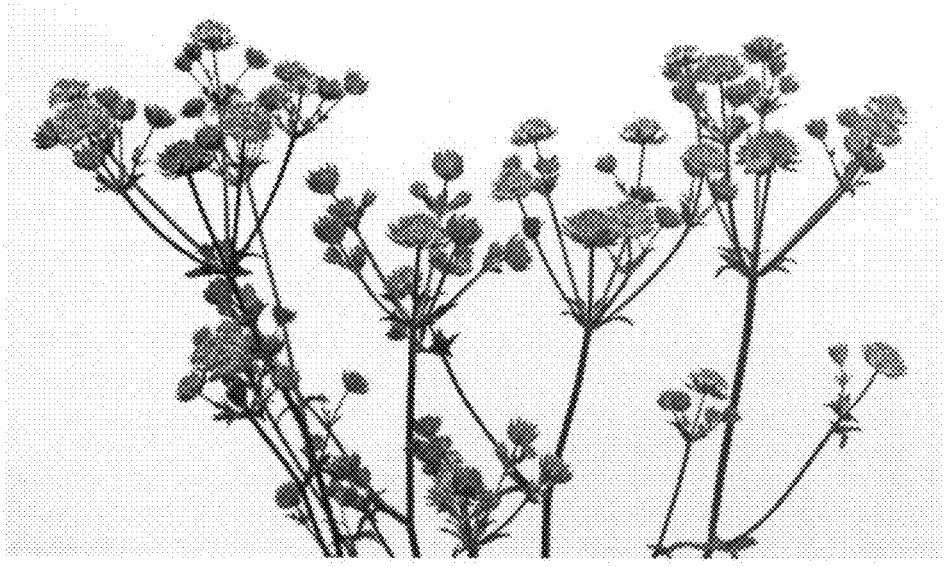

The photograph in FIG. 2 provides a close-up view of the inflorescences of 'Star of Love'.

Figure 3:
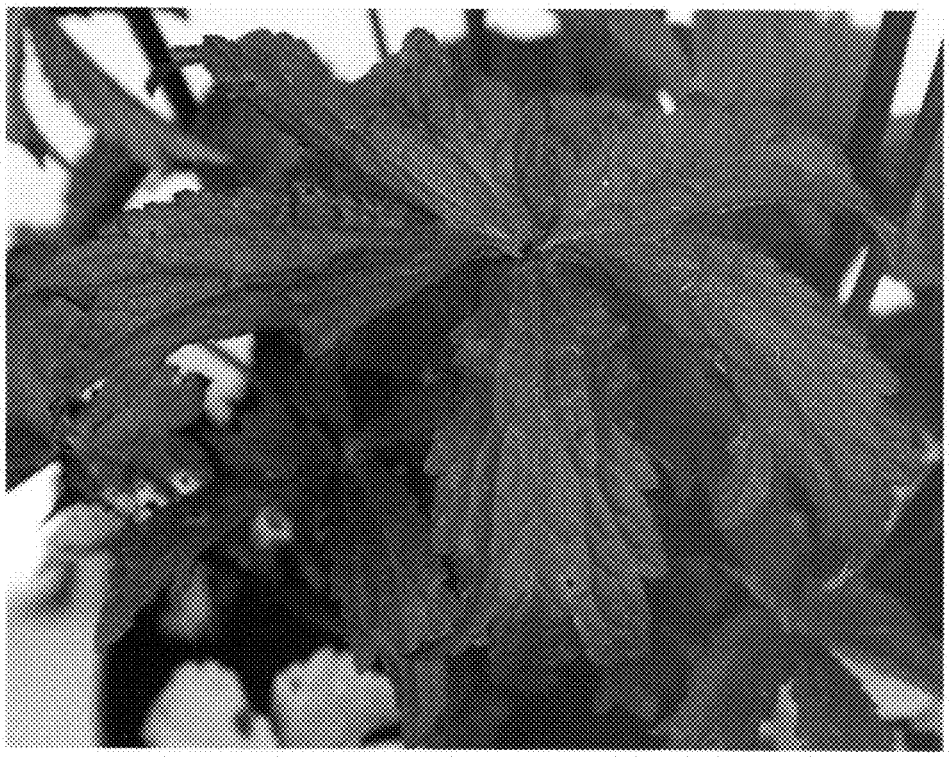

The photograph in FIG. 3 provides a close-up view of the foliage of 'Star of Love'.

The colors in the photographs are as close as possible with the photographic and printing technology utilized and the color values cited in the Detailed Botanical Description accurately describe the colors of the new *Astrantia.*

DETAILED BOTANICAL DESCRIPTION

The following is a detailed description of two year-old plants of the new cultivar as field grown in De Hoef, Netherlands. Plants were grown under average day temperatures ranging from 14° to 26° C. and average night temperatures of 5° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—May to June and again in August to October in The Netherlands.

*Plant type*.—Herbaceous perennial.

*Plant habit*.—Basal rosette with erect flowering stems.

*Height and spread*.—An average of 65.2 cm in height and 38.5 cm in spread.

*Cold hardiness*.—At least to U.S.D.A Zone 6.

*Disease and pest resistance*.—No particular susceptibility and resistance to pest or diseases has been observed.

*Root description*.—Fibrous and fine, 161A in color.

*Propagation*.—Division.

*Crop time*.—About 19 weeks to produce a flowering plant from a division.

*Growth rate*.—Moderate to vigorous.

Stem description:

*Stem shape*.—Rounded.

*Stem color*.—A blend of N186A and 203B with base 143C.

*Stem size*.—An average of 48.4 cm in length (including peduncle) and 4 mm in diameter.

*Stem surface*.—Glabrous and moderately glossy with shallow axial ribs.

*Stem strength*.—Strong.

*Branching habit*.—Stems grow freely from basal rosette, an average of 5 flowering stems per rosette.

*Stem aspect*.—An average angle of 70° to horizontal.

*Internode length*.—An average of 17.1 cm in length (between cauline leaves).

Foliage description:

*Leaf division*.—Simple.

*Leaf shape*.—Palmately parted, with lobes slightly carinate and recurved.

*Leaf base*.—Hastate with lower lobes slightly touching to overlapping.

*Leaf apex*.—Acute.

*Leaf margin*.—Biserrate, teeth aristate.

*Leaf venation*.—Laciniate in pattern, color; upper surface N199A and lower surface 138B.

*Leaf arrangement*.—Basal rosette and alternate cauline leaves.

*Leaf surface*.—Upper and lower surface; glabrous, slightly glossy and rugose.

*Leaf color*.—Young upper surface; 143A and lower surface; a blend between 143C and 144A, mature upper surface; 137B with narrow margins 203B and mature lower surface; a blend between 138B and 147B with narrow margins 203B.

*Leaf size*.—Basal leaves; an average of 9.3 cm in length and 11 cm in width, cauline leaves; an average of 7.5 cm in length and width.

*Leaf number*.—An average of 5 leaves per basal rosette and 2 leaves per stem.

*Petiole*.—Cauline leaves; sheathing and winged, an average of 4.2 cm in length and 7 mm in diameter, color; a blend between 143B and 144A, glabrous surface, basal leaves; ovate in shape, an average of 17 cm in length and 4 mm in diameter, color; 146A suffused with 187B towards the base, glabrous surface.

Flower description:

*Inflorescence type*.—Compound umbel.

*Lastingness of inflorescence*.—An average of 12 days, self-cleaning.

*Lastingness as a cut flower*.—10 to 12 days.

*Harvestable stems per year*.—An average of 10 on a three year-old plant.

*Inflorescence size*.—An average of 2.3 cm in height (excluding peduncle) and 3.5 cm in width.

*Inflorescence fragrance*.—Moderate, typical of *Astrantia major*.

*Flower number*.—An average of 60 flowers per umbel, 29 umbels per compound umbel, and 240 flowers per flowering stem.

*Flower form*.—Single, campanulate.

*Flower aspect*.—Upright and upright-outward.

*Flower size*.—An average of 4 mm in diameter and 7.5 mm in height.

*Flower bud*.—Obovate with flattened apex, an average of 2 mm in length and diameter, color; 59A with base 143B and apex 155A, surface dull and glabrous.

*Petals*.—5, narrow elliptic in shape, recurved, entire margins, narrowly acute apex, an average of 3 mm in length and 0.6 mm in width, dull and glabrous on both surfaces, color; upper surface when opening and when fully open 64A with apex and base NN155C and lower surface when opening and fully open 64B to 64C with apex and base NN155C, color not fading.

*Calyx*.—Rotate, held upright, an average of 2 mm in length and 2.5 mm in diameter.

*Sepals*.—5, narrowly ovate in shape, entire margin, narrowly acute apex, cuneate base, an average of 2 mm in length and 0.8 mm in width, dull and smooth on both surfaces, color; upper and lower surfaces when opening and when fully open 147A with apex 59D.

*Peduncle*.—An average of 4.4 cm in length and 2 mm in diameter, strong in strength, color; a blend between N186C and 200A, primary peduncles held at an average angle of 0° from main stem and secondary peduncles held at an average angle of 40° from main stem, surface glabrous and moderately glossy.

*Pedicel*.—An average of 6 mm in length and 0.2 mm in diameter, strong, color N77B, held at an average angle of 0° (central flowers) and 80° (outer flowers), surface glabrous and moderately glossy.

*Involucral bracts*.—An average of 17 per umbel, obovate in shape, entire margin, acute apex, attenuate base, an average of 1.6 cm in length and 4 mm in width, both surfaces dull and glabrous, color; both surfaces N186D with apex 187A.

Reproductive organs:

*Gynoecium*.—2 pistils, an average of 3.75 mm in length, stigma is club-shaped and N77A in color, style; an average of 3.5 mm in length, N77A in color, ovary; 143A in color with ten ribs 157C.

*Androcoecium*.—5 stamens, anthers are kidney shaped, an average of 0.5 mm in length and NN155C with apex 59D in color, filament; an average of 4 mm in length and 59D in color, pollen is low in quantity and 156D in color.

*Fruit/seeds*.—No fruit or seeds have been observed.

It is claimed:

1. A new and distinct cultivar of *Astrantia* plant named 'Star of Love' as herein illustrated and described.

* * * * *